United States Patent [19]

Rouaud et al.

[11] Patent Number: 5,695,592
[45] Date of Patent: Dec. 9, 1997

[54] METHOD OF ADHESIVELY BONDING MINERAL PARTICLES TO SUPPORTS

[75] Inventors: Thierry Rouaud, Paris; Michel Robin, Poissy, both of France

[73] Assignee: Institut Francais Du Petrole, Rueil Malmaison, France

[21] Appl. No.: 405,866

[22] Filed: Mar. 17, 1995

[30] Foreign Application Priority Data

Mar. 17, 1994 [FR] France .................................. 94 03249

[51] Int. Cl.[6] .................................................. B32B 31/12
[52] U.S. Cl. ...................... 156/279; 427/202; 427/372.2; 427/402
[58] Field of Search ............................... 427/196, 202, 427/372.2, 345, 419.2; 156/89, 278, 279

[56] References Cited

PUBLICATIONS

Tetsuhiko, Manufacture of Semiconductor Fine Particles--Doped Silica Glass, Patent Abstract of Japan, vol. 16, No. 133 (C–0925) (1992) & JP–A–03 295 826 (Seiko Epson Corp.).

*Primary Examiner*—James Engel
*Assistant Examiner*—M. Curtis Mayes
*Attorney, Agent, or Firm*—Pollock, Vande Sande & Priddy

[57] ABSTRACT

Particles are adhesively bond to a support such as a glass or metal strip by covering the support with a film of a sol-gel solution by immersing in a liquid containing an organometallic compound, such as an organic silicon compound. The film is allowed to gel and during gelling, mineral particles are projected against the coated support. The gelled film coated with particles is dried and unbonded particles are removed. The method is of particular application to adhesively bonding clay, carbonate and silica particles.

18 Claims, 2 Drawing Sheets

METHOD OF ADHESIVELY BONDING MINERAL PARTICLES TO SUPPORTS

TECHNICAL FIELD

The invention concerns a method of adhesively bonding mineral particles to supports, in particular planar supports such as glass or metal strips.

BACKGROUND OF THE INVENTION

Hydrocarbon deposits have long been considered to be media which can be wetted by water. Recent studies, however, have shown the existence of hydrophobic zones or zones with heterogeneous wettability. Increasing our knowledge of the wettability of different minerals present in oil deposits is very important as this parameter has a substantial influence on its recovery.

The angle $\theta$ resulting from the thermodynamic equilibrium between three surface tensions $\gamma$ characterises the wettability of a solid S by two fluids L1 and L2 in contact:

$$\gamma \cos \theta = \gamma_{SL2} - \gamma_{SL1}$$

where $\gamma$ is the surface tension between the two fluids L1 and L2, $\gamma_{SL1}$ is the surface tension between the solid S and the fluid L1 and $\gamma_{SL2}$ is the surface tension between the solid S and the fluid L2.

One of the techniques used to measure the contact angle is Wilhelmy's method. This consists of measuring the force exerted by a fluid-fluid interface on a solid surface when the latter is displaced across the interface. If the solid is a planar rectangular strip, the force exerted, expressed in Newtons, is as follows:

$$F = 2(L+E) \gamma \cos \theta + PA + PL$$

where:

2(L+E): Perimeter of the strip, L being the width and E the thickness, in meters;

$\gamma$: Surface tension of fluids (generally liquids) L1 and L2, in Newton/meter;

PA: Buoyancy, in Newton;

PL: Weight of the strip, in Newton.

In practice, F is measured by suspending the strip on the table of a precision balance and vertically displacing the receptacle containing the two liquids. The advantage of Wilhelmy's method is that it provides a profile of the contact angle on the strip surface rather than a single point such as that produced using the static drop technique.

Wilhelmy's method is only generally used for silica using glass strips to study the wettability between water and mineral oils from a deposit. These strips, normally used as microscope slide covers, have the advantage of being available in standard sizes, in large quantities and at little cost.

Unfortunately, a severe problem is encountered in applying Wilhelmy's method to other minerals such as clays or carbonates. It is very difficult, in fact almost impossible, to obtain some minerals in a pure enough form other than as a powder. Even when a solid mineral can be obtained, it must still be sufficiently strong to be able to be cut into pieces of a particular size.

One solution is to bond the mineral particles to a support. However, under the experimental conditions of Wilhelmy's method, the adhesive material binding the particles to the substrate must have qualities which are rarely simultaneously fulfilled by conventional adhesives and resins:

chemical inertia as regards the water and the hydrocarbon;

thermal stability;

resist bonding with the fluids to be measured;

total absence of solvent or additive which could adsorb onto the minerals or migrate into the fluids; and resistance to solvents used for cleaning or drying.

A very simple electrostatic bonding technique can be used for clays. It consists of drying a suspension of clay, which may or may not contain a small quantity of calcium chloride, on the support. This method is currently used to prepare samples for spectroscopic analysis, but has two disadvantages when it comes to the method of determining wettability used in this invention: the first is the problem of ensuring that a given amount of clay is evenly deposited; the second is the uncertainty of the bonding in water and in the hydrocarbon, in particular in the case of alternating immersion in these two fluids.

SUMMARY OF THE INVENTION

We have now discovered a method of adhesively bonding mineral particles to supports which can be planar, such as glass or metal strips, using a "sol-gel" method. Using the method of the invention, a thin layer of an organometallic compound is deposited which acts as the bonding adhesive. After drying, the binder between the particles and the support is constituted solely by a metallic oxide. Problems of organic pollution and chemical inertia no longer exist and there is the additional benefit of the thermal stability of the metal oxide.

BEST AND VARIOUS MODES FOR CARRYING OUT INVENTION

Figure 1:
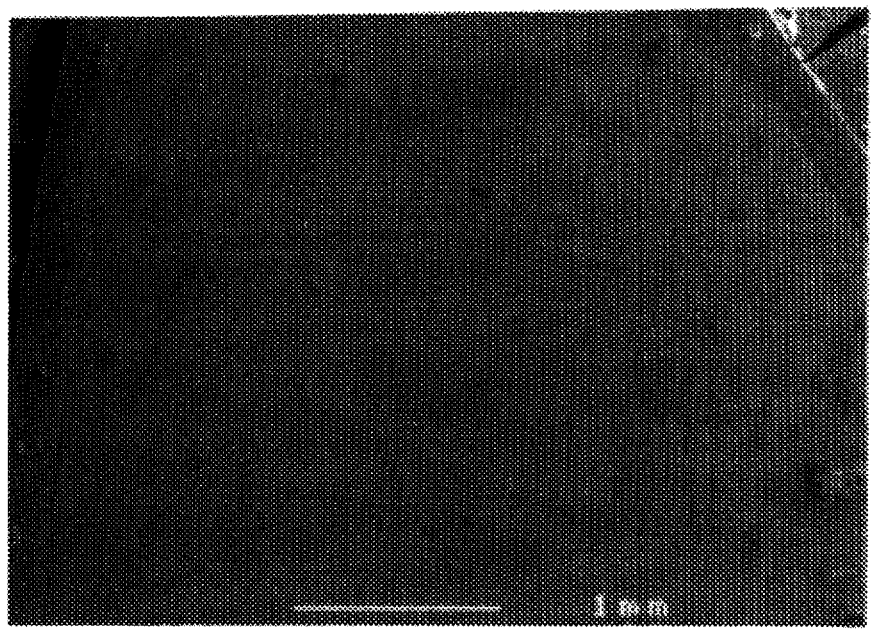
FIGS. 1–4 are micro-photographs.
Figure 2:
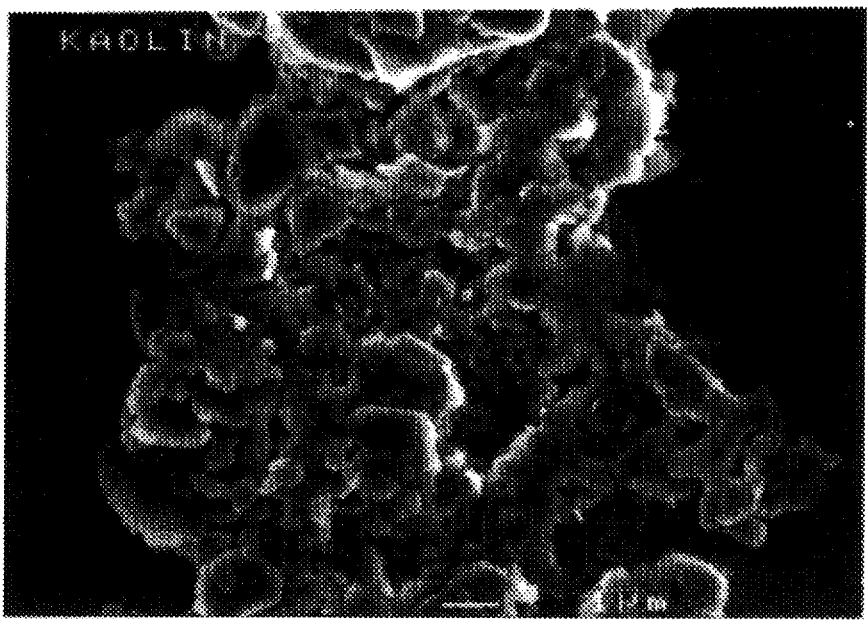
Figure 3:
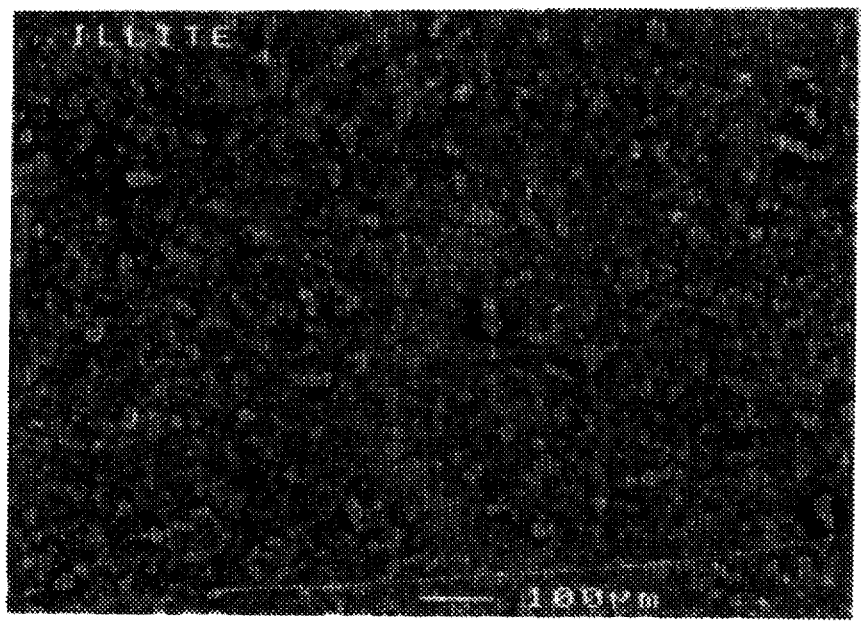

It is known that the sol-gel method can be used to produce glasses or ceramics from organic molecular compounds which react at low temperature in a liquid medium, as compared with conventional glasses which are formed by high temperature fusion of oxides.

This method uses the hydrolysis and condensation reactions of metal alkoxides. These compounds have general formula $M(-O-R)_m$ where M is a metal (silicon, aluminium, titanium . . . ), m is the coordination number, -O-R is an alkoxy radical bonded to the metal via an oxygen atom and alkyl chain R has general formula: $C_nH_{(2n+1)}$. The hydrolysis reaction can be written as:

$$M(-OR)_m + H_2O \rightarrow HO\text{-}M(O\text{-}R)_{m-1} + R\text{-}OH$$

The compound formed reacts by causing the following condensation reaction:

$$M(-OR)_m + HO\text{-}M(O\text{-}R)_{m-1} \rightarrow (RO\text{-})_{m-1}M\text{-}O\text{-}M(-OR)_{m-1} + R\text{-}OH$$

or

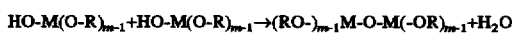

$$HO\text{-}M(O\text{-}R)_{m-1} + HO\text{-}M(O\text{-}R)_{m-1} \rightarrow (RO\text{-})_{m-1}M\text{-}O\text{-}M(-OR)_{m-1} + H_2O$$

The sum of the two reactions gives:

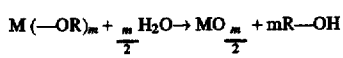

It is also possible to produce, for example, silica ($SiO_2$), alumina ($Al_2O_3$), or titanium oxide ($TiO_2$) in which case M is Si, Al or Ti respectively.

On the microscopic level, the different phases of the method are as follows: in a starting "sol" containing a solvent, the metal alkoxide and water, the first step is the formation of polymeric clusters. The hydrolysis and condensation reactions cause their size to increase and a gel starts to form. The time required, at room temperature, can be several minutes to several tens of days, depending on the initial constituents and the experimental conditions. The gel obtained is then dried at room temperature or by gentle heating to eliminate the solvent(s) and the reaction products: during this phase, it loses more than 50% of its initial volume. The sol-gel bonds to the support (glass, metal) by reaction between the O-H groups of the surface and the partially hydrolysed metal alkoxide:

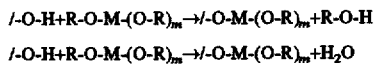

The method of the invention is generally defined as follows:

a) a support, which may be planar and may be constituted by a glass strip or a metal strip, is covered with a film of sol-gel solution by immersion in a liquid containing an organometallic compound;

b) the film gels and, during gelling, the mineral particles which are to be bonded to the film are projected onto the coated support, for example using a jet of compressed air;

c) the gelled film which is covered with particles is dried and the unbonded particles are removed.

The different steps of the method of the invention will be described below in more detail, referring particularly to a planar support.

The supports used can be glass strips or metal strips of various metals or alloys, such as steels.

Immersion step a) is carried out by totally or partially immersing the support in a solution comprising an organometallic compound which can be, for example, an organic silicon, titanium or aluminium compound. It may be, for example, a tetraalkylorthosilicate such as tetraethylorthosilicate, or a tetraalkylorthotitanate such as tetraethylorthotitanate.

The solution is usually a hydroalcoholic solution containing, for example, at least 70% by volume of alcohol (in particular ethanol) and acidified water, acidified with hydrochloric acid, for example.

The tetralkylorthosilicate concentration in the solution is generally 5% to 20% by volume.

The strip is held vertically and is at least partially immersed in the solution, then pulled vertically out of the solution, preferably at a constant speed, to produce a film with a constant thickness. The pulling speed of the strip can be 100 to 1000 mm/minute. The thickness of the resulting liquid deposited increases with the traction speed. It is generally such that the thickness of the dry deposit is 0.5 to 1.5 micrometers.

It is possible to coat just one surface of the strip with the sol-gel film. This is effected by masking the surface to be protected, for example with an adhesive plastic film which prevents the gel from fixing to this surface.

The sol-gel film deposited on at least one of the support surfaces gels in the second step b) of the method. If an organic silicon compound is used, for example tetraethylorthosilicate, the gelling reaction can be written as follows:

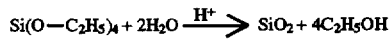

During gelling in the second step b), the mineral particles are bonded, for example by introducing the strip into a chamber in which the mineral particles to be bonded are in motion. The average size of these particles can be from several tens of micrometers to several hundreds of micrometers (for example, 5 to 75 micrometers), depending on the material under consideration. The strip is rotated inside the chamber, for example at a rate of 200 to 500 revolutions/minute, and a jet of compressed gas (for example air) is injected into the chamber at a pressure of 4 to 8 Pa, for example, for several seconds. A portion of the particles moving inside the chamber will adhere to the surface of the sol-gel film.

To avoid the formation of particle aggregates, the maximum size of the particles to be adhesively bonded can be controlled. This can be carried out by interposing a sieve with a suitable mesh size between the moving strip and the particles.

In step c), the strip is dried, for example at room temperature, for a period of, for example, 6 to 24 hours. The excess of unbonded particles are then removed by an appropriate method: the strip can, for example, be subjected to ultrasound vibrations for about 1 minute, for example, in a washing liquid, which can be distilled water, an alcohol, or a liquid hydrocarbon, which may be chlorine-containing, depending on the nature of the particles and their final destination. Finally, the strip can be rinsed, for example with ethanol, and stored away from dust.

Using the method of the invention described above, a large fraction of the strip surface can be covered with particles. The coating ratio can be adjusted by modifying the experimental parameters. A 70% coverage may be selected, for example.

Particular particles which can be bonded to planar supports using the method of the invention are clay particles (such as kaolin or illite), carbonate particles (such as calcite or dolomite) or silica particles.

It is also possible to bond mineral particles which have an organic film on their surface, for example those taken from crude oil, which film is fixed for example by deposition or adsorption or by chemically modifying the particle surface, for example by silane grafting (using hexadecyltrichlorosilane, for example).

In general, strips covered with mineral powders using the adhesive bonding method of the invention are used for wettability tests using two fluids, for example oil and water. In this instance, it is generally advantageous to remove any impurities which run the risk of changing the wetting characteristics. To this effect, thorough cleaning is thus carried out, Strips coated with carbonates can thus be cleaned with ozone under ultraviolet irradiation; clay coatings can be cleaned using an aqueous solution of hydrogen peroxide; and silica coatings can be cleaned using a sulphonitric or sulphochromic mixture or using ozone under ultraviolet irradiation.

These treatments do not affect the adhesion of the particles to the strip.

In addition, the wettability of the mineral surfaces formed by the adhesively bonding method of the invention can be modified, for example to render a hydrophilic mineral surface wettable by hydrocarbons.

This can be effected by grafting, adsorption or deposition of organic compounds.

Thus silanes can be grafted onto a sol-gel or a sol-gel coated with silica.

Organic compounds, for example crude oil, or solutions of asphaltenes in toluene, can be adsorbed onto strips coated with clay, calcite or silica. The bonding of the mineral particles (clays, carbonates, silica, etc) is not altered during or after contact with these media.

The following examples illustrate the invention.

Glass strips used as microscope slide covers were used as the supports. Their dimensions were 30 mm×24 mm×0.15 mm.

In each experiment, the strip was held at one of its ends by a plastic support which was split in the middle and extended by a metal rod.

A hydroalcoholic solution containing 20% by weight of tetraethylorthosilicate, acidified with hydrochloric acid, was used.

The glass strip was partially immersed in the solution and pulled vertically out of it at a constant rate of 500 mm per minute.

Gelling was rapid: the tetraethylorthosilicate transformed into silica and the alcohol (ethanol) and water were eliminated by evaporation.

The strip was quickly transferred to a chamber, fixed to a plastic support which was split in the middle and extended by a metal rod connected to a motor.

The strip was rotated and the mineral particles, already in the chamber, were brought into suspension by means of a jet of compressed air produced at the bottom of the chamber.

A fraction of the particles became fixed to the sol-gel film as it gelled.

The particle-coated strip was removed from the chamber and dried at room temperature for 12 hours. Excess particles were then removed using ultrasound vibrations in an ethanol bath.

This method was used to adhesively bond kaolin, illite and calcite particles.

Figure 4:
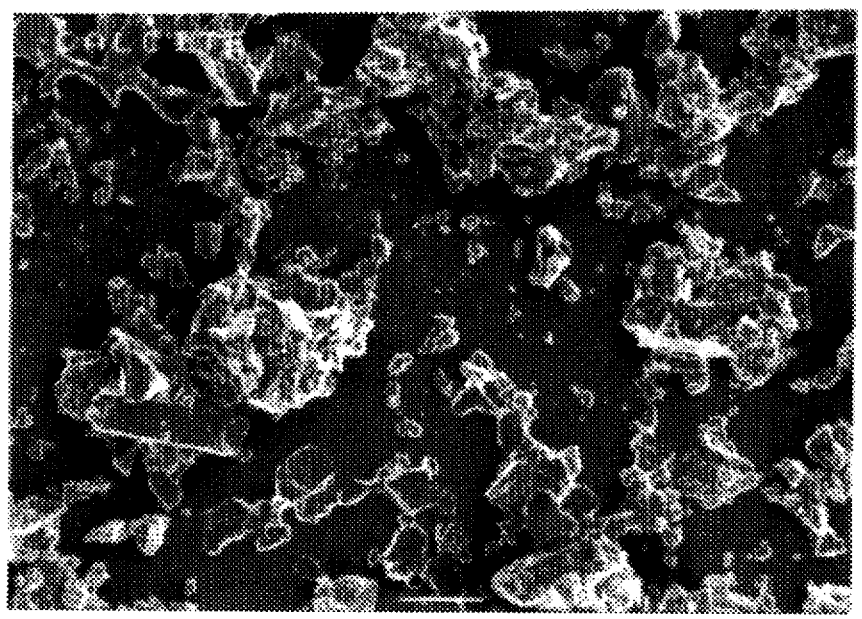

Accompanying FIGS. 1 to 4 are microphotographs obtained using a scanning electron microscope:
- of the sol-gel surface with no particle deposition (FIG. 1);
- of a surface after adhesively bonding kaolin particles (FIG. 2) in which the average size of the bonded particles can be measured (about 5 micrometers);
- of a surface after adhesively bonding illite particles (FIG. 3: average particle size 25 to 65 micrometers); and
- of a surface after adhesively bonding calcite particles (FIG. 4: average particle size 1 to 20 micrometers).

We claim:

1. A method of adhesively bonding mineral particles to a support, which comprises:
    a) a step in which at least one of the surfaces of said support is covered with a film of sol-gel solution by immersing the support in a liquid containing an organometallic compound;
    b) a step in which said film gels and mineral particles to be bonded are projected against the film during gelling; and
    c) a step in which the particle-coated film is dried and unbonded particles are removed.

2. A method according to claim 1, characterised in that said support is planar.

3. A method according to claim 2, characterized in that said support consists of a glass strip or a metal strip.

4. A method according to claim 2, characterized in that the organometallic compound is a tetraalkylorthosilicate.

5. A method according to claim 2, characterized in that, in step a), the immersed support is pulled vertically at a constant speed of 100 to 1000 mm per minute, to coat said support with a film with a thickness which corresponds to a dry deposit thickness of 0.5 to 1.5 micrometers.

6. A method according to claim 1, characterised in that said support consists of a glass strip or a metal strip.

7. A method according to claim 6, characterized in that the organometallic compound is a tetraalkylorthosilicate.

8. A method according to claim 6, characterized in that, in step a), the immersed support is pulled vertically at a constant speed of 100 to 1000 mm per minute, to coat said support with a film with a thickness which corresponds to a dry deposit thickness of 0.5 to 1.5 micrometers.

9. A method according to claim 1, characterised in that the organometallic compound is a tetraalkylorthosilicate.

10. A method according to claim 9, characterized in that, in step a), the immersed support is pulled vertically at a constant speed of 100 to 1000 mm per minute, to coat said support with a film with a thickness which corresponds to a dry deposit thickness of 0.5 to 1.5 micrometers.

11. A method according to claim 9, characterised in that said tetraalkylorthosilicate is tetraethylorthosilicate.

12. A method according to claim 11, characterized in that, in step a), the immersed support is pulled vertically at a constant speed of 100 to 1000 mm per minute, to coat said support with a film with a thickness which corresponds to a dry deposit thickness of 0. to 1.5 micrometers.

13. A method according to claim 1, characterised in that, in step a), the immersed support is pulled vertically at a constant speed of 100 to 1000 mm per minute, to coat said support with a film with a thickness which corresponds to a dry deposit thickness of 0.5 to 1.5 micrometers.

14. A method according to claim 1, characterised in that, in step b), the particles are bonded to the support coated with the film by rotating said support in a chamber in which said particles are in motion.

15. A method according to claim 14, characterised in that, in step b), the support is rotated at a speed of 200 to 500 revolutions per minute and the particles are moved by entrainment in a jet of compressed gas.

16. A method according to claim 14, characterised in that, in step b), a sieve with a mesh size which can prevent protection and adherence of aggregates of particles is placed between the particles to be moved and the rotating support.

17. A method according to claim 14, characterised in that the particles to be bonded are several tens of micrometers to several hundreds of micrometers in size.

18. A method according to claim 1, characterised in that, in step c), the unbonded particles are eliminated after drying by subjecting the coated support to ultrasound vibrations in a washing liquid.

* * * * *